(12) United States Patent
Shetty

(10) Patent No.: US 11,040,063 B2
(45) Date of Patent: Jun. 22, 2021

(54) COMPOSITION FOR STRENGTHENING THE IMMUNE SYSTEM AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 387 days.

(21) Appl. No.: 16/142,290

(22) Filed: Sep. 26, 2018

(65) Prior Publication Data

US 2019/0022137 A1 Jan. 24, 2019

Related U.S. Application Data

(60) Provisional application No. 62/563,928, filed on Sep. 27, 2017.

(51) Int. Cl.

| | | |
|---|---|---|
| *A61K 33/24* | (2019.01) | |
| *A61K 35/644* | (2015.01) | |
| *A61K 9/107* | (2006.01) | |
| *A61K 9/00* | (2006.01) | |
| *A23L 21/25* | (2016.01) | |
| *A23L 33/16* | (2016.01) | |
| *A23L 33/105* | (2016.01) | |
| *A61P 37/04* | (2006.01) | |
| *A61K 36/28* | (2006.01) | |
| *A61K 36/59* | (2006.01) | |
| *A61K 36/484* | (2006.01) | |
| *A61K 36/39* | (2006.01) | |
| *A23L 5/00* | (2016.01) | |
| *A61K 36/882* | (2006.01) | |
| *A61K 47/46* | (2006.01) | |
| *A61K 36/232* | (2006.01) | |
| *A61K 47/02* | (2006.01) | |

(52) U.S. Cl.
CPC ............ *A61K 33/24* (2013.01); *A23L 5/00* (2016.08); *A23L 21/25* (2016.08); *A23L 33/105* (2016.08); *A23L 33/16* (2016.08); *A61K 9/006* (2013.01); *A61K 9/0053* (2013.01); *A61K 9/0095* (2013.01); *A61K 9/1075* (2013.01); *A61K 35/644* (2013.01); *A61K 36/232* (2013.01); *A61K 36/28* (2013.01); *A61K 36/39* (2013.01); *A61K 36/484* (2013.01); *A61K 36/59* (2013.01); *A61K 36/882* (2013.01); *A61K 47/02* (2013.01); *A61K 47/46* (2013.01); *A61P 37/04* (2018.01); *A23V 2002/00* (2013.01)

(58) Field of Classification Search
CPC .... A61K 2300/00; A61K 36/59; A61K 33/10; A61K 33/26; A61K 33/30; A61K 33/34; A61K 36/53; A61K 36/67; A61K 36/68; A61K 36/81; A61K 36/8965; A61K 36/9066; A61K 36/9068; A61K 36/232; A61K 36/28; A61K 36/39; A61K 36/484; A61K 36/882; A61K 45/06; A61K 35/644; A61K 33/24; A61K 47/02; A61K 47/46; A61K 9/0053; A61K 9/006; A61K 9/0095; A61K 9/1075; A23L 21/25; A23L 33/10; A23L 33/105; A23L 33/16; A23L 5/00; A61P 35/02; A61P 35/00; A61P 37/04; A61P 39/06; A23K 50/90; A23V 2002/00

See application file for complete search history.

(56) References Cited

U.S. PATENT DOCUMENTS

| | | | |
|---|---|---|---|
| 2011/0052731 A1* | 3/2011 | Park ................. | A61K 36/28 424/728 |
| 2019/0022150 A1* | 1/2019 | Shetty .............. | A61K 35/644 |

OTHER PUBLICATIONS

Chauhan SM, Farooqui A, Trivedi A "Plants foraged by bees for honey production in northern India: The diverse flora of India and its implications for apiculture" Acta Palaeobotanica, Apr. 2017, 57(1),pp. 119-132; doi: 10.1515/acpa-2017-0003 (Year: 2017).*
Zohara Y; Michal Rudich "Chapter 9: Medicinal Herbs as a Potential Source of High-Quality Honeys" Bee Products: Properties, Applications, and Apitherapy, Mizrahi A and Lensky Y (ed.), 1997, 269pp. (Chapters 9: pp. 77-81); doi: 10.1007/978-1-4757-9371-0. (Year: 1997).*
Campos MG, Cunha A; MArkham KR "Chapter 12: Bee-Pollen: Composition, Properties, Applications" Bee Products: Properties, Applications, and Apitherapy, Mizrahi A and Lensky Y (ed.),1997, 269pp. (pp. 93-99); doi: 10.1007/978-1-4757-9371-0. (Year: 1997).*
Kumar R and Chaudhary OP ("Bee Plants in India" Khadi Gramodyog, Aug.-Sep. 1993, 34(11-12), pp. 844-854 (Year: 1993).*
Paul "Blood compatibility studies of *Swarna bhasma* (gold bhasma), an Ayurvedic drug" Int J Ayurveda Res. Jan.-Mar. 2011, 2(1),pp. 14-22; doi: 10.4103/0974-7788.83183 (Year: 2011).*
The Government of India, Biological Diversity Act, 2002.†

\* cited by examiner
† cited by third party

*Primary Examiner* — Aaron J Kosar
(74) *Attorney, Agent, or Firm* — Piloff Passino & Cosenza LLP; Sean A. Passino; Rachel K. Piloff

(57) ABSTRACT

Composition for strengthening the immune system and method of preparation of the same are disclosed herein. The disclosed herbal composition includes gold particles and honey which facilitate in boosting the immune system and overall health. It is believed to improve the physical and mental health of an individual. The disclosed composition is instrumental as immune stimulating and memory boosting agent.

13 Claims, 7 Drawing Sheets

COMPOSITION FOR STRENGTHENING THE IMMUNE SYSTEM AND METHOD OF PREPARATION THEREOF

CROSS REFERENCE TO RELATED APPLICATION

This application is based on and claims the benefit of U.S. Provisional Application 62/563,928 filed on the 27 of Sep. 2017, the contents of which are incorporated herein by reference in their entirety.

TECHNICAL FIELD

The embodiments disclosed in this specification relates to a composition capable of strengthening the immune system, and more particularly to its immunomodulatory effects. It also relates to the process of preparation of such composition.

BACKGROUND

A healthy life devoid of diseases or discomfort is a sign of an efficient immune system. An efficient and resilient immune system is an indicator that the body is well capable of defending itself against physical and environmental challenges. Therefore, it is of prime importance that good care be taken to strengthen our immune system.

The environmental challenges faced by the human body from time to time, exposes the immune system to new antigens, thus helping the immune system to strengthen itself by building defense against the exposed antigens. Thus, over time, the immune system progressively educates itself to combat pathogens and infections. Body's exposure to factors such as stress, pollution, metabolic disorders, virus, poor diet, lifestyle, etc however, weakens the body and its efficiency to combat external stress. Therefore, it is important that the immune system be supported by offering nutritious balanced diet, physical activity, alcohol and smoke free lifestyle, etc.

In modern times, avoiding factors such as pollution and stress can be challenging. Therefore, many look forward to adopting ways of enhancing or strengthening the body's defense mechanism. Inclusion of immunity and health boosting ingredients in one's diet is one of the ways to better health. Ingredients like ginger, liquorice, tulsi are age old medicines known for boosting immunity and rejuvenating the human body.

Ayurveda, through its traditional methods, teaches the use of herbs to boost immunity by improving digestion, slowing the aging process, eliminating toxins, improving blood circulation, etc. Factors such as improved digestion, blood circulation and elimination of toxins, collectively, can have a positive impact on the immune system. Ayurveda, to some extent, is also believed to reverse the harmful effects of pollution, stress, etc on the human body.

Many compositions claiming to rejuvenate and revitalize body are known. However, there exists a need for an effective method for boosting one's immune system and overall health.

OBJECTS OF THE DISCLOSED EMBODIMENTS

The principal object of the embodiments disclosed herein is to provide a composition having immunomodulatory activity and a method for its preparation Another object of the embodiments disclosed herein is to provide method for boosting the immune system and overall health.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which.

DETAILED DESCRIPTION

Figure 1:
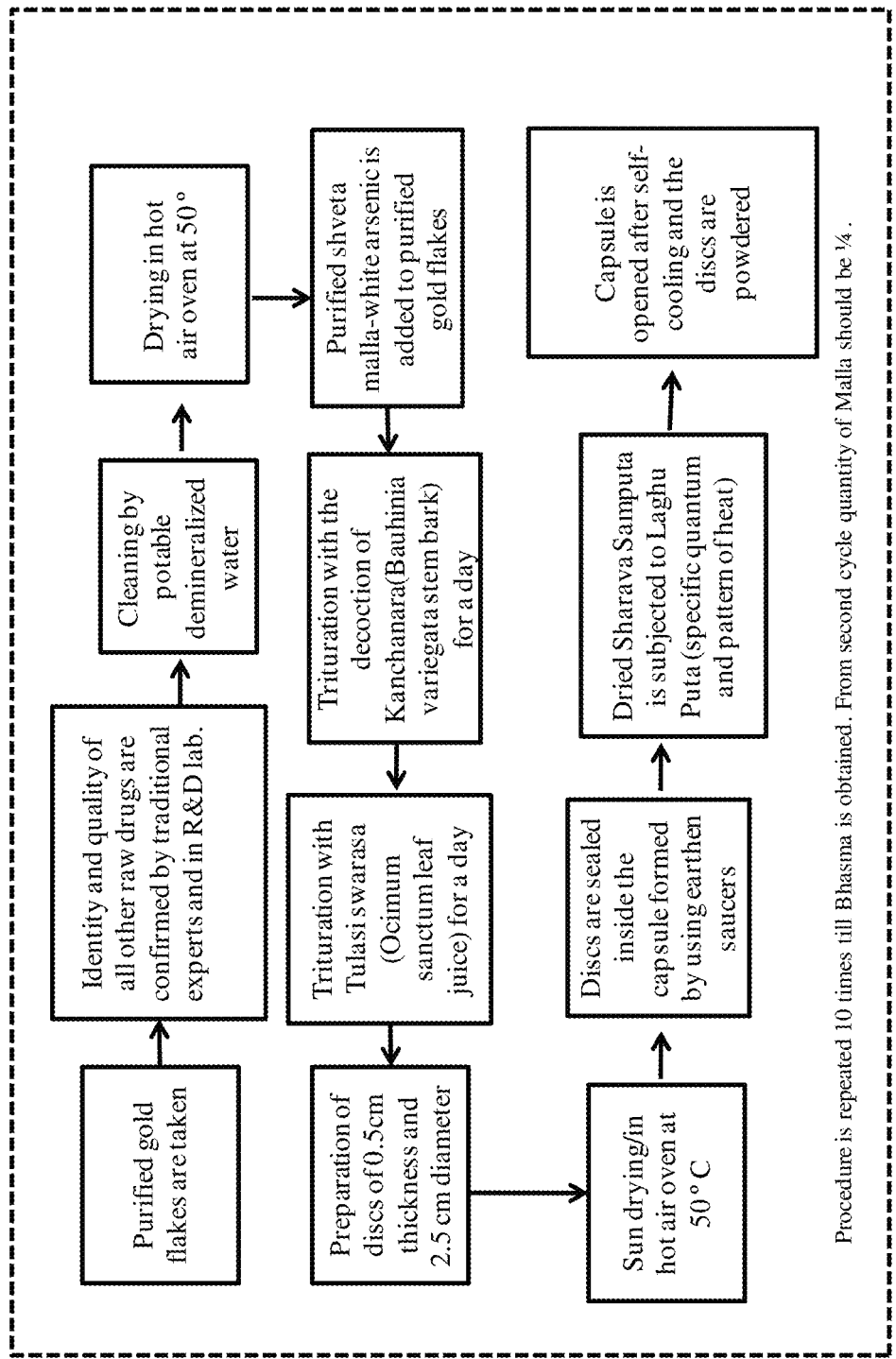
FIG. 1 depicts a flowchart for the preparation of Swarna Bhasma.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a composition of therapeutic value, and a process for the preparation of the composition. The embodiments of the herbal composition disclosed herein is useful as an immune system and overall health booster. It is further useful in improving the overall quality of life. In the various embodiments herein, overall health includes physical and mental health of children and adults. The disclosed composition finds use as an immunomodulator/immunostimulant and antioxidant. Accordingly, the embodiments disclosed herein achieve a method of boosting the immune system and overall health of an individual.

Composition

The disclosed embodiments herein provide a composition having gold particles and medicated honey. In an embodiment, the gold particles are incinerated gold flakes or Swarna bhasma. In another embodiment, the herbal composition includes Swarna bhasma and medicated honey. Further, the amount of Swarna bhasma that may be included is any amount generally known to be effective in such compositions. In an embodiment, Swarna bhasma or gold particles are present in the composition in an amount in the range of 0.1 to 0.2 wt. %. In other embodiments, the disclosed composition may further include other suitable additives.

Swarna Bhasma

In an embodiment, the gold particles are processed swarna bhasma. In an embodiment, the processed swarna bhasma is prepared by triturating swarna bhasma in herb extracts. In another embodiment, the herb extracts may include extracts of atleast one of *Saussurealappa, Acorus calamus, Convolvulus pluicaulis, Tylophora indica, Murraya koinigi, Cynodon dactylon, Glycerrhiza glabra, Tinospora cordifolia* and *Centella asiatica*. The extracts of the herbs maybe in the form of a decoction or fresh juice. In an embodiment, the extract includes a decoction of *Saussurea lappa, Acorus calamus* and *Glycerrhiza glabra*; and fresh juice of *Convolvulus pluicaulis, Tylophora indica, Murraya koinigi, Cynodon dactylon, Tinospora cordifolia* and *Centella asiatica*. The herbs may alternatively be used in any other form such as concentrates, pellets, powder or other dried forms, etc. Table 1 illustrates a list of herbs instrumental in processing of Swarna bhasma.

TABLE 1(a)

List of herbs for processing swarnabhasma.

| No. | Botanical name | Sanskrit name | Form |
|---|---|---|---|
| 1 | *Saussurea lappa* | Kushtha | Decoction |
| 2 | *Acorus calamus* | Vacha | Decoction |
| 3 | *Convolvulus pluicaulis* | Shankhapushpi | Fresh juice |
| 4 | *Tylophora indica* | Arkapushpi | Fresh juice |
| 5 | *Murraya koinigi* | Kaidarya | Fresh juice |
| 6 | *Cynodon dactylon* | ShvetaDurva | Fresh juice |
| 7 | *Glycerrhiza glabra* | Yashtimadhu | Decoction |
| 8 | *Tinospora cordifolia* | Guduchi | Fresh juice |
| 9 | *Centella asiatica* | Mandookaparni | Fresh juice |

Honey

In an embodiment, the honey is specially cultured medicated honey. In an embodiment, the specially cultured honey is achieved by bee keeping in gardens having selected medicinal plants possessing anticancer, antioxidant, antimicrobial and anti-inflammatory properties. In another embodiment, the medicated honey is such that it includes anti-cancer properties.

In an embodiment, the honey is obtained by feeding honey bees with bee feed obtained from at least one of the following medicinal plant: *Plumeria rubra, Vincarosea, Ageretum conzyoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*. In an embodiment, the medicated honey is extracted from hives/honey supers of honey bees fed with bee feed obtained from medicinal plants. The honey may be extracted from hives/honey supers by methods generally known in the field. In an embodiment, the bee feed may include nectar of medicinal plants. In another embodiment, the bee feed may include an extract obtained from the medicinal plants.

The Disclosed composition, in the various embodiments herein, may further include a suitable additive. The list of suitable additives includes solvents, binders, lubricants, herbal carriers, other therapeutic substances, oils and salts that are generally known in the art.

The composition disclosed herein may be formulated in various dosage forms such that it is suitable for oral administration. The herbal composition may be in the form of tablets, pellets, lozenges, granules, capsules, solutions, emulsions, suspensions, or any other form suitable for use. In an embodiment, the herbal composition is formulated in the form of nano-emulsion. In an embodiment, the composition may be a composition having the characteristics as that described in Table 1(b). In another embodiment, the composition may be a composition having the nutritional value as that illustrated in Table 1(c). Various modifications to the disclosed embodiments will be apparent to those skilled in the art, and the general principles discussed herein may be applied to other embodiments and applications without departing from the scope of the invention. Therefore, the invention is not intended to be limited to the embodiments disclosed herein.

TABLE 1(b)

Characteristics of the composition.

| TEST PARAMETERS | SPECIFICATIONS |
|---|---|
| Description | Golden brown colored viscous liquid |
| Identification | Positive for gold, flavonoids, sugars (fructose and glucose) |
| Moisture, % | 5.4% |
| HMF, mg kg−1 | 00 |
| Free acidity, meq kg−1 | 14 |
| pH | 4.17 |
| Ash, % (w/w) | 0.11 |
| Diastase activity (Gothe units) | 13.77 |
| Color, mm Pfund | 40.33 |
| Scanning Electron Microscopy | Presence of micro gold particles ranging from 3 to 6μ at 5000× and nano particles ranging from 88 to 206 nm at 50000× magnification, scattered pollen grains |

TABLE 1(c)

Nutritional value of the composition
NUTRITIONAL VALUE OF THE TEST PRODUCT:
Serving Size 4 drops (0.2 gm)

| | Amount per serving | Range |
|---|---|---|
| Calories | 0.61 kcal | |
| Calories from fat | 0 | |
| Total Fat | 0 | 0 |
| Cholesterol | 0 | 0 |
| Sodium | 0.08 mg | 0.02-0.06% |
| Potassium | 0.104 mg | 0.050-0.055% |
| Total Carbohydrates | 0.164 g | 80-85% |
| Dietary fiber | 0.06 mg | 0.02-0.04% |
| Protein | 0.06 mg | 0.02-0.04% |
| Vitamin | 0.001 mg | 0.0004-0.0006% |
| Calcium | 0.012 mg | 0.004-0.006% |
| Iron | 0.00084 mg | 0.0004-0.00045% |

TABLE 1(c)-continued

Nutritional value of the composition
NUTRITIONAL VALUE OF THE TEST PRODUCT:
Serving Size 4 drops (0.2 gm)

| | Amount per serving | Range |
|---|---|---|
| Magnesium | 0.004 mg | 0.001-0.002% |
| Phosphorous | 0.008 mg | 0.003-0.005% |
| Gold | 0.4 mg | |

Method

Disclosed herein are embodiments of a method of preparing the Disclosed composition. In an embodiment, the method includes processing gold particles by triturating with a herb extract, and triturating the processed gold particles with medicatedhoney. The gold particles instrumental in the various embodiments herein may be in the form of Swarna bhasma prepared by any methods generally known in the field. Following are examples, by way of illustration only, of a method for the preparation of Swarna bhasma. The method includes purification and incineration of gold.

Example 1—Purification (Shodhana) of Gold

Gold flakes were heated on a gas blower up to red hot and quenched sequentially in Tila Taila (sesame oil), Takra (butter milk), Gomutra (cow urine), Aranala (sour gruel), and Kulattha Kwatha (decoction of horse gram—Dolichos biflorus seeds) for seven times each respectively.

Panchamrittika (a combination of brick, hematite, rock salt, mud of anthill and plant ash) was made into paste with juice of *Citrus medica* Linn by trituration in Khalvayantra (mortar and pestle). Accurately weighed gold flakes were cut into small pieces (about 4" length) and each gold flake was smeared properly with the above paste on both side and kept for drying for three days. After complete drying of paste, material was kept in the Sharava (earthen pot) and covered with another earthen pot. Then the junction was sealed with the paste of fuller's earth and cloth. The seal was then properly dried and Kapota Puta (a specific quantum of heat provided by burning 8 cow dung cakes). After self-cooling the Samputa was taken out and carefully opened. The wrapped substances of Swarna Patra (gold flake) was removed by rubbing with clean cloth carefully on both side and washed with warm water.

Example 2—Incineration of Gold

Purified gold flakes were taken and dried in a hot air oven at about 50° C. Purified white arsenic was added to purified gold flakes. Further, it was triturated with a decoction of *Bauhinia variegate* stem bark, preferably for a day. It was then triturated with *Ocimum sanctum* leaf juice, preferably for a day. The obtained mass was further prepared into discs of 0.5 cm thickness and 2.5 cm diameter and sun dried at about 50° C. Discs were further sealed inside the capsule formed by using earthen saucers. Dried sharava samputa was subjected to Laghu puta following which capsule was opened after self-cooling and discs were powdered. This procedure was repeated ten times until bhasma was obtained. From the second cycle the quantity of white arsenic was $1/4^{th}$. FIG. 1 illustrates the method for the incineration of gold.

In an embodiment, the herb extract includes fresh juice/decoctions obtained from atleast one of the following herbs: *Saussurea lappa, Acorus calamus, Convolvulus pluicaulis, Tylophora indica, Murraya koinigi, Cynodon dactylon, Glycerrhiza glabra, Tinospora cordifolia* and *Centella asiatica* (as depicted in Table 1(a)). In an embodiment, the swarna bhasma (or gold particles) may be triturated in each of the herb extracts, separately, one by one till it dries up. In another embodiment, the swarna bhasma may be triturated with a mixture of extracts obtained from the herbs depicted in Table 1(a).

In an embodiment, triturating processed swarna bhasma (or gold particles) with medicated honey includes adding small quantities of honey to processed swarna bhasma (or gold particles) and triturating slowly until homogeneity and desired characteristics are attained. In an embodiment, processed swarna bhasma may be triturated in medicated honey to obtain a nano-emulsion.

In an embodiment, the method of producing medicated honey includes providing honeybees with bee feed obtained from medicinal plants having anti-cancer and anti-oxidant properties; and extracting the honey produced by the honeybees. The bee feed used may include nectar and/or herb extract/decoction of medicinal plants. In an embodiment, the bee feed is plant nectar of atleast one of *Plumeria rubra, Vinca rosea, Ageretum conzyoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*. The bee feed may alternatively or additionally include a herb extract obtained from atleast one of *Plumeria rubra, Vinca rosea, Ageretum conzyoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*. In an embodiment, the herb extract may be obtained by techniques generally known in the art such as grinding, extraction, boiling, centrifugation, etc, of one or more medicinal plants.

In an embodiment, the method includes maintaining a controlled condition. The controlled condition may be conditions that are generally considered suitable for honeybees to produce honey. In an embodiment, the controlled conditions include maintaining a temperature in the range of 32° C. and 36° C. and relative humidity of about 75%, for a preferable period of about 120 days. It would be apparent to a person skilled in the art that many modifications in the method may be practiced without departing from the scope of the present invention.

Honey extraction may be performed by method generally known in the field. In an embodiment, extracting honey includes removing honey super, looking for brood and managing appropriately, moving honey into hot houses and extracting honey using an extractor. The honey supers, after extraction may further be stored or returned to the hive. In an embodiment extraction of honey may be performed by generally known extractors.

Figure 3:
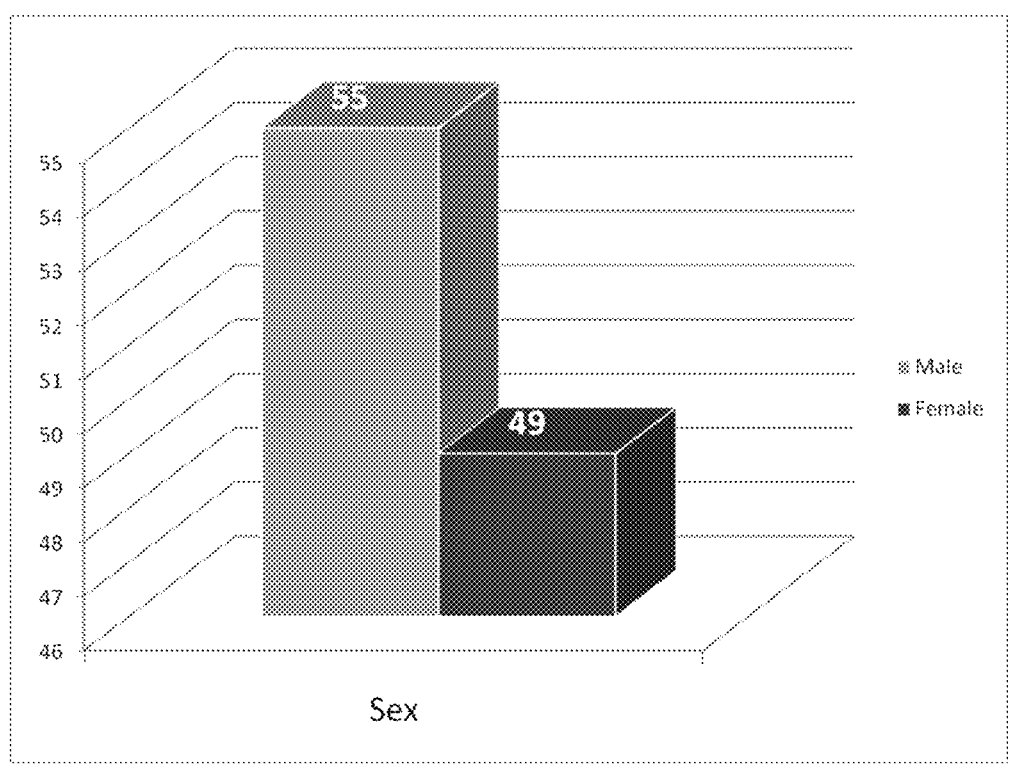
FIG. 3 is a graph depicting the sex ratio of the subjects in the study.

The honey produced according to the various embodiments herein may further be processed by method generally known in the field. In an embodiment, processing may be performed by techniques such as heating directly or indirectly, straining, filtration, etc. In a preferred embodiment, the raw honey is filtered and then heated under controlled conditions. Controlled conditions may be conditions suitable to purify and prevent honey from granulation. In one embodiment, controlled conditions for processing include controlled temperature of about 61° C. to 63° C., for a maximum period of about 30 minutes and until the humidity is within the range of 18% to 22%. In an embodiment, heating is performed to ensure pasteurization and may be performed by using a power blanket or direct heat. It would be apparent to a person skilled in the art that many modifications in the method may be practiced without departing from the scope of the present invention. FIG. 3 depicts a flowchart for method of processing medicated honey as disclosed in the various embodiments herein.

Treatment

Disclosed herein are embodiments of a method for improving the overall health. Also disclosed are embodiments of a method for boosting the immune system. The embodiments of the disclosed composition may also be instrumental as a memory boosting agent. Furthermore, various embodiments of the disclosed composition may also be useful as an antioxidant. In an embodiment, the method includes administering to a subject a composition having gold particles and medicated honey, wherein the gold particles are processed by trituration with herb extracts of herbs such as *Saussurea lappa, Acorus calamus, Convolvulus pluicaulis, Tylophora indica, Murraya koinigi, Cynodon dactylon, Glycerrhiza glabra, Tinospora cordifolia* and *Centella asiatica*; and medicated honey is specially cultured honey.

The subject in the embodiments herein may include children and adult. The dosage of the composition may vary depending on the subject. The composition may be administered in serving sizes of 1 to 4 drops. In an embodiment, the composition may be administered to subjects above the age of 5 years in serving size of 4 drops having dosage strength of 0.4 mg. In another embodiment, the composition may be administered to subjects below the age of 5 years in serving size of 2 drops having dosage strength of 0.2 mg. Embodiments of the disclosed composition (also referred as Test drug) was subjected to toxicity study. The Test drug was observed to fall under Category-5 in the Globally Harmonized System (GHS), the hazard category defined by: 2000 mg/kg<LD50<5000 mg/kg.

Embodiments of the disclosed composition (also referred as Test drug) was further evaluated for its immunostimmulant properties in Swiss albino mice. The invention is further described by reference to the following examples by way of illustration only, and should not be construed to limit the scope of the present invention. It will be apparent to those skilled in the art that many modifications, both to materials and methods, may be practiced without departing from the scope of the present invention.

Example 3—Pre-Clinical Study

The objective was to determine the immunostimulant property of "Test drug" in male swiss albino mice. The immunostimulant property of "Test drug" was studied using cell mediated immune response.

Test drug descriptions: Dosage form: Liquid; Color: Golden brown; Physical state: Viscous liquid, Odour: Pleasant; Taste: Sweet and astringent; Storage: Original container at room temperature.

Method description: Species: Mice; Strain: Swiss albino; Sex: Male; Age/weight at start of test: 10-12 weeks/25-30 g b.wt; No of animals:6/group; Acclimatization period: Acclimatized for 7 days prior to dosing; Housing: Individually in polyurethane cages with no other species being housed in the same room; Husbandry: A 12-h light/12-h dark artificial photoperiod was maintained. Room temperature 22° C.). (±3°) and relative humidity 50-70%; Feed and Water: Animals had free access to pelleted feed. (Nutrilab rodent, Tetragon ChemiePvt Ltd., India). Reverse osmosis (Rios, USA) purified water ad libitum; Identification: Animals were kept in individual cages and cage cards numbered as follows.

Control: 101, 102, 103, 104, 105, 106
Test drug (Low): 201, 202, 203, 204, 205, 206
Test drug (High): 301, 302, 303, 304, 305, 306

Experimentation Details: Groups/treatment regimen: Control group:Vehicle-Honey; Test group: Test drug (0.5 and 1.0 ml/kg b.wt, p.o); Dose: 0.5 and 1.0 ml/kg, b.wt; Route of administration: Oral; Frequency of administration: Once daily for 14 days (Pretreatment); Duration of the experiment: 20 days;

Primary immunization: $15^{th}$ day with SRBC (Sheep red blood cells), i.p; Secondary immunization: $19^{th}$ day with SRBC (Sheep red blood cells), s.p Methods: Cell mediated immune function was assessed by delayed type hypersensitivity (DTH) test. DTH response was determined using the method of Raisuddin et al., 1991. Mice were pretreated for a period of two weeks with vehicle or "Test drug" (0.5 and 1.0 ml/kg b.wt, p.o) and were challenged with 0.2 ml of 10% sheep red blood cells (SRBC), i.p. on 15th day. On fifth day of immunization, the mice were again challenged with 1×108 cells sub plantar in left hind footpad. The right footpad was injected with normal saline which served as control. Increase in footpad thickness will be measured 24 h after the challenge.

Observations:

Body weight: Body weight was recorded on the day of initiation of the experiment and once a week thereafter.

Paw edema: Increased in footpad thickness were measured 24 h after injection of SRBC using plethysmometer (Singa, Taiwan). The increase in edema volume of SRBC injected paw was compared with the normal saline injected paw.

Serum biochemistry: On the day of termination, the blood was collected from retro-orbital plexus, hematology parameters were analyzed using fully automated hematology analyzer (PE6000) and Serum glutamate oxaloacetate transaminase (SGOT) and Serum glutamate pyruvate transaminase (SGPT) levels were determined using semi-automated biochemical analyzer (Star 21 plus, Aspen Diagnostics Pvt. Ltd., India).

Gross necropsy: The animals were subjected to gross pathological observation on the day of termination of the experiment.

Organ weight: Lymph organs such as spleen, liver and kidney were collected and weighed. Relative organ weight of each organ was determined and compared with the control.

Statistical analysis: Values were expressed in mean±SEM. Statistical analysis was performed using GraphPad Prism Software 4.0 version, USA. Mean differences between the groups were compared by one way ANOVA followed by Dunnett's multiple comparison of all columns". p value <0.05 was fixed as statistical significance criterion Results:

Body weight: No significant difference was observed between the control and test drug administered groups. Table. 2 depicts the effect of Test drug on body weight in the experimental animals.

TABLE 2

| | | Body weight (g) | | |
|---|---|---|---|---|
| Group | Treatment | Day 0 | Day 7 | Day 14 |
| I | Control (0.5% CMC) | 31.20 ± 0.86 | 32.40 ± 0.75 | 33.40 ± 0.68 |
| II | Test drug (0.5 ml/kg) | 31.40 ± 0.75 | 31.60 ± 0.24 | 33.20 ± 0.20 |
| III | Test drug (1.0 ml/kg) | 31.40 ± 0.60 | 31.00 ± 0.45 | 32.20 ± 0.37 |

Values were expressed in mean ± SEM, n = 5;
Significance with Dunnet multiple comparison test following one way ANOVA was indicated as *P < 0.05 and **P < 0.01 vs control group Paw edema: Treatment with Test drug showed significant increase in footpad thickness of SRBC injected paw when compared to vehicle treated mice dose dependently. This indicates the immunostimulant effect of the test drug. Table.3 depicts the effect of Test drug on paw edema volume in the experimental animals.

TABLE 3

| Group | Treatment | Footpad thickness (mm) |
|---|---|---|
| I | Control (0.5% CMC) | 0.05 ± 0.01 |
| II | Test drug (0.5 ml/kg) | 0.08 ± 0.00* |
| III | Test drug (1.0 ml/kg) | 0.09 ± 0.01** |

Values were expressed in mean ± SEM, n = 5;
Significance with Dunnet multiple comparison test following one way ANOVA was indicated as *P < 0.05 and **P < 0.01 vs control group Hematology analysis: No significant difference was observed in the hematological parameters between groups. Table. 4 depicts the effect of Test drug on hematological parameters in the experimental animals.

TABLE 4

| Group | Treatment | HGB (%) | RBC ($10^6$/µl) | WBC ($10^3$/µl) |
|---|---|---|---|---|
| I | Control (0.5% CMC) | 13.40 ± 0.78 | 5.94 ± 0.74 | 6.43 ± 0.90 |
| II | Test drug (0.5 ml/kg) | 13.60 ± 0.51 | 6.33 ± 0.69 | 6.16 ± 0.48 |
| III | Test drug (1.0 ml/kg) | 13.38 ± 2.06 | 6.06 ± 1.00 | 5.86 ± 0.77 |

Values were expressed in mean ± SEM, n = 5;
Significance with Dunnet multiple comparison test following one way ANOVA was indicated as *P < 0.05 and **P < 0.01 vs control group Serum biochemistry: No Significant change in SGOT and SGPT value was observed between the experimental animals. Table. 5 depicts the effect of Test drug on serum biochemistry in the experimental animals.

TABLE 5

| Group | Treatment | SGOT (U/I) | SGPT (U/I) |
|---|---|---|---|
| I | Control (0.5% CMC) | 59.53 ± 10.41 | 48.64 ± 4.24 |
| II | Test drug (0.5 ml/kg) | 54.40 ± 4.57 | 41.04 ± 2.57 |
| III | Test drug (1.0 ml/kg) | 55.27 ± 4.61 | 41.46 ± 3.09 |

Values were expressed in mean ± SEM, n = 5;
Significance with Dunnet multiple comparison test following one way ANOVA was indicated as *P < 0.05 and **P < 0.01 vs control group Gross necropsy: No gross pathological changes were observed in the experimental animals.

Relative organ weight: No significant difference in relative organ weight was observed between the vehicle and test drug administered mice. Table. 6 depicts the effect of Test drug on relative organ weight in the experimental animals.

TABLE 6

| | | Relative organ weight (g) | | |
|---|---|---|---|---|
| Group | Treatment | Spleen | Liver | Kidney |
| I | Control (0.5% CMC) | 0.56 ± 0.01 | 5.63 ± 0.10 | 1.38 ± 0.05 |
| II | Test drug (0.5 ml/kg) | 0.58 ± 0.01 | 5.40 ± 0.41 | 1.27 ± 0.09 |
| III | Test drug (1.0 ml/kg) | 0.48 ± 0.06 | 6.11 ± 0.32 | 1.33 ± 0.07 |

Values were expressed in mean ± SEM, n = 5;
Significance with Dunnet multiple comparison test following one way ANOVA was indicated as *P < 0.05 and **P < 0.01 vs control group Conclusion: In the above tested condition, "Test drug" was herein found to possess the potent immunostimulatory effect on male swiss albino mice when administered at the dose level of 50 mg/kg b.wt, p.o.

Example 2—Clinical Study 104 children were randomly selected the study.

Aim and objective of the study: To see the efficacy of Test drug in preventing disorder in children. To see efficacy of Test drug in reducing the disease frequency in children.

Source for study: OPD Kaumarabhritya, MIAMS, Manipal. MIAMS Kutumba Sadasya Clinics.

Sample Size: 104 children undergoing Test drug were included in the study.

Design of Study: Single group

Dose of Test drug: 2 drops for age below 5 years and 4 drops for age above 5 years.

Methodology: The survey proforma was given to the parents for providing the information. Proforma had question related to many aspects of the drug, administration, taste, observed changes, school performances and their opinion. Questions were framed to get the data related to information before Test drug administration and after administration. The parents were asked to fill forms of survey proforma and submitted to the concerned centre. Then the data was collected and put in the master chart for analysis.

Inclusion criteria: Children who have undergone 6 consecutive Test drug; Children who have taken only Test drug; Children under the age of 16 years.

Exclusion criteria: Children who have not been administered 6 doses of Test drug; Children who have administered other than Test drug for Swarna Prashana; Children who lapse the dose of Test drug.

Assessment criteria: Following manifestations are observed for assessments

1. Respiratory system: Common cold, Sneezing, Cough, Breathing difficulty, Head ache, Fever.
2. Gastro Intestinal System: Loss of appetite, Distension of abdomen, Vomiting, Loose stools, Hard stools, Abdominal pain, Mucus with stools.
3. Developmental problems.
4. Scholastic work performances.
5. Behavioural Adjustments with classmates.
6. Behavioural Adjustments with teachers.
7. Behavioural Adjustments with parents.
8. Subject understanding ability.

The $1^{st}$, $2^{nd}$ and $3^{rd}$ criteria were graded under the following uniform scoring pattern.

Always—4, Frequently—3, Occasionally—2, Not Present—1, Absent—0.

The $4^{th}$, $5^{th}$, $6^{th}$, $7^{th}$ and $8^{th}$ criteria were graded under the following uniform scoring pattern:
Poor—01, Moderate—02, Excellent—03

The data was put in the master chart which has all information of 104 children and analyzed statistically using various tests Observations: Following observations were found from 104 children who had undergone Test drug administration:

58 (55.77%) children were below the age of 5 years and 46 (44.23%) children were above 5 years of age. Sex ratio showed male children were 55 (52.88%) and female children were 49 (47.12%) in number. In majority cases i.e, 63 (60.58%) cases it was observed that mother was the informant.

Figure 2:
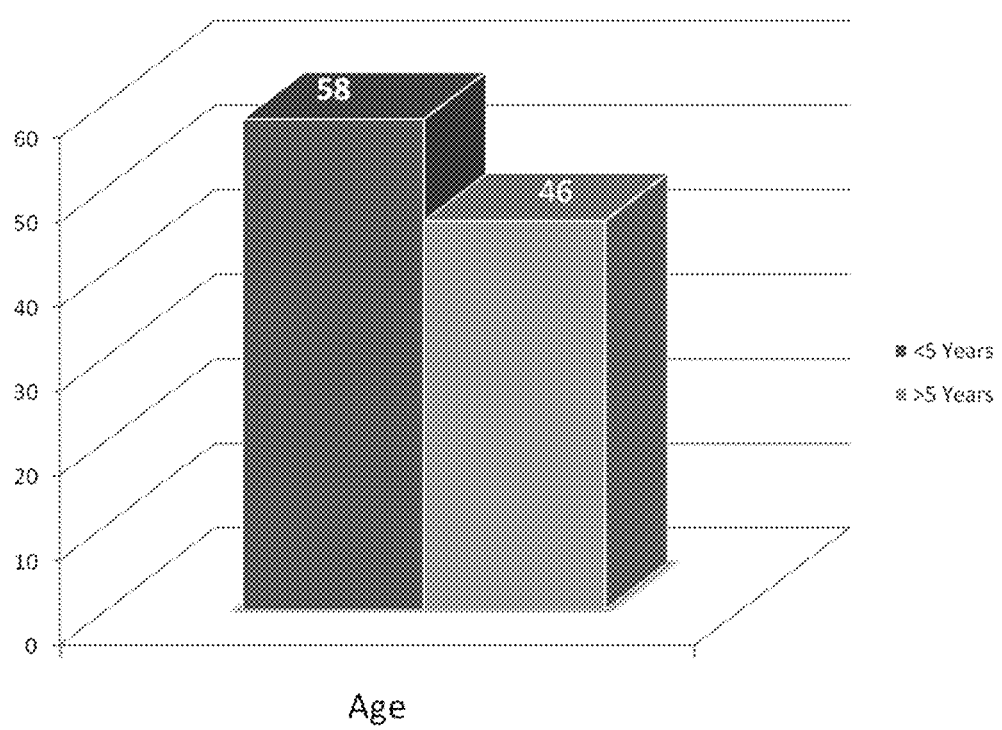
FIG. 2 is a graph depicting the age group of the children in the study.

80 (76.92%) children mentioned that the Test drug is sweeter in taste. This indicates the palatability of the drug. The drug had no refusal for administration in 103 (99.04%) children. 59 (56.73%) children were school going children. Table. 7 depicts the Age groups of children in the study. FIG. 2 is a graphical representation of the age groups of children in the study.

TABLE 7

| Sl. No. | Age | No. of children | % |
|---|---|---|---|
| 1 | Below 5 years | 58 | 55.77 |
| 2 | Above 5 years | 46 | 44.23 |

Table. 8 depicts the sex ratio of children in the study. FIG. 3 is a graphical representation of the sex ratio of children in the study.

TABLE 8

| Sl. No. | Sex | No. of children | % |
|---|---|---|---|
| 1 | Male | 55 | 52.88 |
| 2 | Female | 49 | 47.12 |

Figure 4:
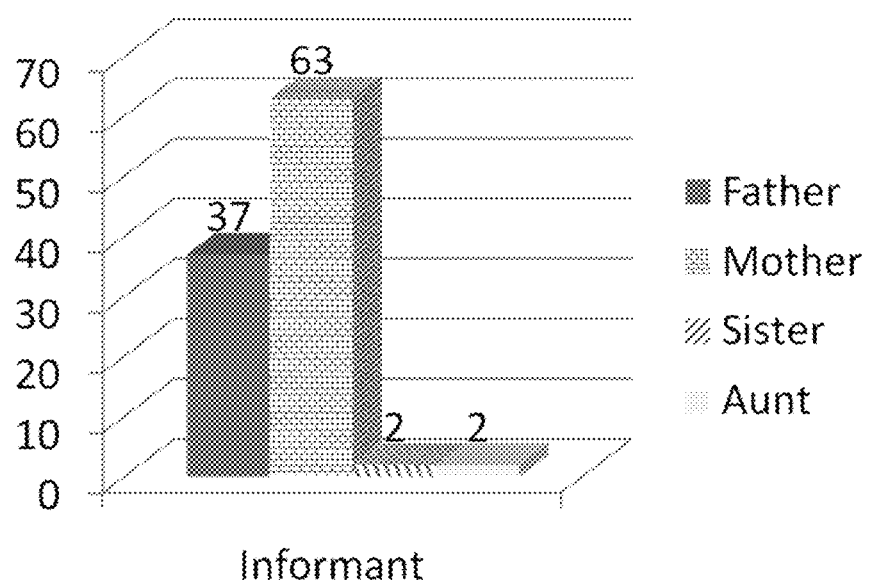
FIG. 4 is a graph depicting the percentage of Informant who filled the survey forms of Test drug clinical survey.

Table. 9 depicts the percentage of Informant who filled the survey forms of Test drug clinical survey. FIG. 4 is a graphical representation of the percentage of Informant who filled the survey forms of Test drug clinical survey.

TABLE 9

| Sl. No. | Informant | Number | % |
|---|---|---|---|
| 1 | Father | 37 | 35.58 |
| 2 | Mother | 63 | 60.58 |
| 3 | Sister | 2 | 01.92 |
| 4 | Aunt | 2 | 01.92 |

Figure 5:
FIG. 5 is a graph depicting the taste of Test drug as stated by the Children.

Table. 10 depicts the taste of Test drug as stated by the Child. FIG. 5 is a graphical representation of the taste of Test drug as stated by the Child.

TABLE 10

| Sl. No. | Taste | No. of children | % |
|---|---|---|---|
| 1 | Sweet | 80 | 76.92 |
| 2 | Bitter | 1 | 00.96 |
| 3 | Not Mentioned | 23 | 22.12 |

Figure 6:
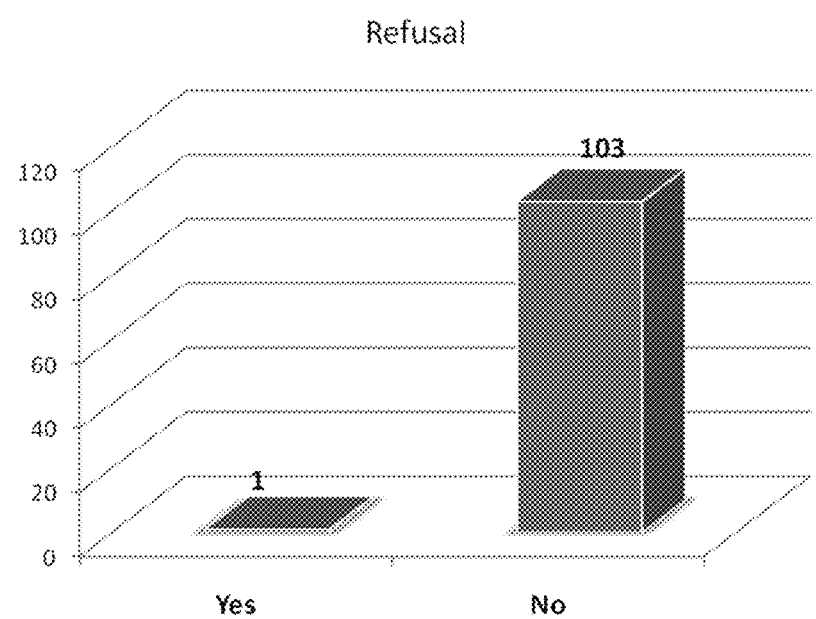
FIG. 6 is a graph depicting the refusal for Test drug administration.

Table. 11 depicts the refusal for Test drug administration. FIG. 6 is a graphical representation of the refusal for Test drug administration.

TABLE 11

| Sl. No. | Refusal | Number | % |
|---|---|---|---|
| 1 | Yes | 1 | 00.96 |
| 2 | No | 103 | 99.04 |

Figure 7:
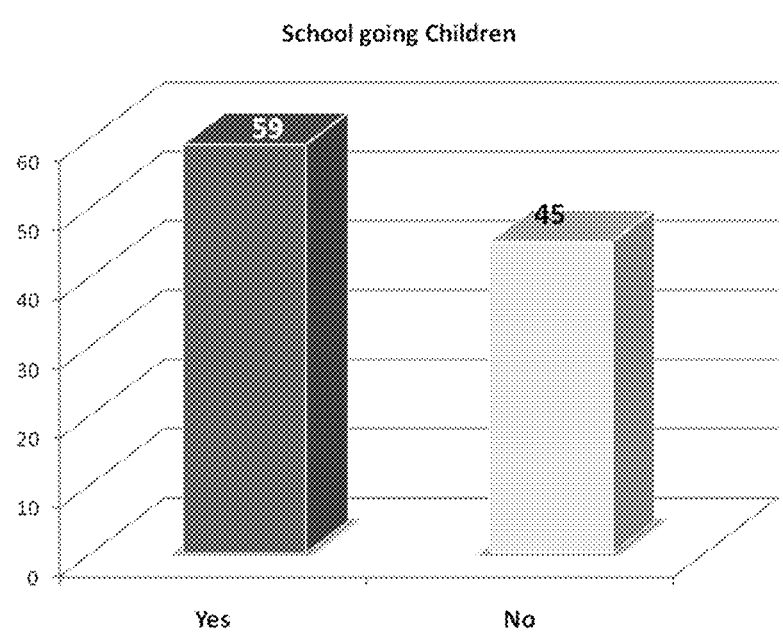
FIG. 7 is a graph depicting the number of school going children in the study; according to embodiments as disclosed herein.

Table. 12 depicts the no. of school going children. FIG. 7 is a graphical representation of the no. of school going children.

TABLE 12

| Sl. No. | School going | Number | % |
|---|---|---|---|
| 1 | Yes | 59 | 56.73 |
| 2 | No | 45 | 43.27 |

Results: In the study, the data was analyzed statistically and following results were obtained. Data Before administration of Test drug and the data obtained from the clinical survey were analyzed by applying paired t tests on different parameters of respiratory system, GIT and behavioral parameters.

Analysis of data on Respiratory system manifestations shows high statistical significance for all parameters—cold, sneezing, head ache, cough, dyspnea and fever. Table. 13 depicts the analysis of data on Respiratory system manifestations.

TABLE 13

| Sl. No. | Parameter | n | Mean | SD | SE | 't' Value | df | P Value |
|---|---|---|---|---|---|---|---|---|
| 1 | Cold | 87 | 0.7701 | 1.0081 | 1.1081 | 7.125 | 86 | <0.001 |
| 2 | Sneezing | 58 | 0.7586 | 1.0141 | 0.1332 | 5.697 | 57 | <0.001 |
| 3 | Head ache | 43 | 0.3488 | 0.6504 | 0.0992 | 3.517 | 42 | <0.001 |
| 4 | Cough | 77 | 0.7922 | 1.0555 | 0.1203 | 6.586 | 76 | <0.001 |
| 5 | Dyspnoea | 41 | 0.4390 | 0.8381 | 0.1309 | 3.354 | 40 | <0.001 |
| 6 | Fever | 69 | 0.8116 | 0.9436 | 0.1136 | 7.144 | 68 | <0.001 |

Table. 14 depicts the analysis of no. of children with respiratory symptoms. Results show reduction in the occurrence of respiratory manifestations by the administration of Test drug.

TABLE 14

| | | No. of children having symptoms | |
|---|---|---|---|
| Sl. No. | Parameter | Before administration of Test drug | On the Date of Survey |
| 1 | Cold | 87 | 73 |
| 2 | Sneezing | 58 | 50 |
| 3 | Head ache | 43 | 38 |
| 4 | Cough | 77 | 66 |
| 5 | Dyspnoea | 41 | 36 |
| 6 | Fever | 69 | 55 |

Analysis of data on GIT manifestations shows high statistical significance in the parameter loss of appetite; moderate significance in the parameters distension of abdomen and abdominal pain; statistical insignificance in parameters vomiting, hard stools, loose stools, mucus with stools. Table. 15 depicts the analysis of data on GIT manifestations.

TABLE 15

| Sl. No. | Parameter | n | Mean | SD | SE | 't' Value | df | P Value |
|---|---|---|---|---|---|---|---|---|
| 1 | Loss of appetite | 75 | 0.4267 | 1.0157 | 0.1173 | 3.638 | 74 | <0.001 |
| 2 | Distension of abdomen | 42 | 0.2857 | 0.8050 | 0.1242 | 2.300 | 41 | <0.05 |
| 3 | Abdominal pain | 54 | 0.4444 | 1.1438 | 0.1556 | 2.855 | 53 | <0.01 |
| 4 | Vomiting | 47 | 0.1702 | 0.8423 | 0.1229 | 1.385 | 46 | >0.05 |
| 5 | Hard stools | 43 | 0.1163 | 0.6252 | 0.0953 | 1.220 | 42 | >0.1 |
| 6 | Loose stools | 43 | 0.1163 | 0.5859 | 0.0894 | 1.301 | 42 | >0.1 |
| 7 | Mucus with stools | 43 | 0.2558 | 0.8478 | 0.1293 | 1.979 | 42 | >0.05 |

Table 16 depicts the analysis of the number of children with GIT symptoms. Table shows reduction in the occurrence of GIT manifestations by the administration of Test drug.

TABLE 16

| | | No. of children | |
|---|---|---|---|
| Sl. No. | Parameter | Before administration of Test drug | On the Date Survey |
| 1 | Loss of appetite | 75 | 66 |
| 2 | Distension of abdomen | 42 | 36 |
| 3 | Abdominal pain | 54 | 46 |
| 4 | Vomiting | 47 | 42 |
| 5 | Hard stools | 43 | 40 |
| 6 | Loose stools | 43 | 38 |
| 7 | Mucus with stools | 43 | 39 |

Analysis of data on behavioral assessments shows high statistical significance in parameter school work performance and subject understanding ability, Moderate significance in the parameter behavioral adjustments with classmates, statistical insignificance in the parameters behavioral adjustment with teacher and parents. Table. 17 depicts the analysis of data on behavioral assessments.

TABLE 17

| Sl. No. | Parameter | n | Mean | SD | SE | 't' Value | df | PValue |
|---|---|---|---|---|---|---|---|---|
| 1 | School work performances | 56 | 0.1786 | 0.4309 | 0.0576 | 3.101 | 55 | <0.005 |
| 2 | Behavioural adjustments with classmates | 56 | 0.1071 | 0.3121 | 0.0417 | 2.569 | 55 | <0.02 |
| 3 | Behavioural adjustments with teacher | 56 | 0.071 | 0.3223 | 0.0431 | 1.658 | 55 | >0.1 |
| 4 | Behavioural adjustments with parents | 56 | 0.018 | 0.3010 | 0.0402 | 0.444 | 55 | >0.1 |
| 5 | Subject understanding ability | 56 | 0.1786 | 0.3865 | 0.0516 | 3.458 | 55 | <0.001 |

Observation: The Test drug is found safe and immunostimulating by the experimental studies. Analysis of data on Respiratory system manifestations shows high statistical significance for all parameters—cold, sneezing, head ache, cough, dyspnea and fever. Test drug is very much beneficial in reducing the symptoms of respiratory manifestations. Test drug is beneficial in preventing the respiratory manifestations, hence it can be concluded that Test drug increases the immunity of the child. This is due to action of Gold in enhancing the nonspecific immunity and action over the inflammation of respiratory system mucosa.

Analysis of data on GIT manifestations shows high statistical significance in the parameter loss of appetite; moderate significance in the parameters distension of abdomen and abdominal pain; statistical insignificance in parameters vomiting, hard stools, loose stools, mucus with stools. Test drug is beneficial in increasing the appetite of children.

Analysis of data on behavioral assessments shows high statistical significance in parameter school work performance and subject understanding ability, Moderate significance in the parameter behavioral adjustments with classmates, statistical insignificance in the parameters behavioral adjustment with teacher and parents. Test drug is beneficial in increasing the intelligence; thinking ability, subject understanding ability. Test drug acts as Medhya Rasayana. The Swarna bhasma has the nootropic property by which the cognitive and behavioral functions are found with significant changes.

Conclusion: The aforementioned studies show that the Test drug is beneficial in enhancement of physical and mental health of children. It is found that the drug is beneficial in enhancing the immunity of the child. The drug was found safe to use. The results were found significant in the prevention and control of respiratory, GIT, and behavioral parameters.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral composition for strengthening the immune system of mammals, comprising processed gold particles obtained by triturating gold particles with herb extract comprising extracts of *Saussurea lappa, Acorus calamus, Convolvulus pluricaulis, Tylophora indica, Murraya koenigii, Cynodon dactylon, Glycyrrhiza glabra, Tinospora cordifolia* and *Centella asiatica*; and medicated honey obtained from honeybees fed with bee-feed obtained from at least one plant selected from a group consisting of *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*, wherein said processed gold particles are present in the range of 0.1 to 0.2 wt. % of the total composition.

2. The composition as claimed in claim 1, wherein said herb extract comprises a decoction of *Saussurea lappa*, a decoction of *Acorus calamus*, fresh juice of *Convolvulus pluricaulis*, fresh juice of *Tylophora indica*, fresh juice of *Murraya koenigii*, fresh juice of *Cynodon dactylon*, a decoction of *Glycyrrhiza glabra*, fresh juice of *Tinospora cordifolia* and fresh juice of *Centella asiatica*.

3. The composition as claimed in claim 1, wherein said medicated honey is obtained from honeybees fed with bee-feed obtained from *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*.

4. The composition as claimed in claim 3, wherein said bee-feed comprises of nectar of *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*.

5. The composition as claimed in claim 1, wherein said composition is formulated as a nano-emulsion.

6. The composition as claimed in claim 1, wherein said composition is in the form of oral drops.

7. A method for the preparation of composition claimed in claim 1, said method comprising:
   processing gold particles by triturating in herb extract comprising extracts of *Saussurea lappa, Acorus calamus, Convolvulus pluicaulis, Tylophora indica, Murraya koinigi, Cynodon dactylon, Glycerrhiza glabra, Tinospora cordifolia* and *Centella asiatica*; and
   triturating the processed gold particles with medicated honey.

8. The method as claimed in claim 7, wherein said medicated honey is extracted from hives of honeybees fed with bee-feed obtained from at least one medicinal plant selected from a group consisting of *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*.

9. The method as claimed in claim 8, wherein said bee-feed comprises of nectar of at least one medicinal plant selected from a group consisting of *Plumeria rubra, Vinca rosea, Ageratum conyzoides, Calotropis gigantea, Calotropis procera, Nerium indicum, Thevetia neriifolia, Jasminum officinale, Jasminum auriculatum, Musa paradisiaca, Jasminum humile, Nyctanthes arbor-tristis, Ocimum sanctum, Ocimum gratissimum, Tabernaemontana divaricata, Tridax procumbens, Cassia auriculata, Hibiscus vitifolius, Sesbania grandiflora, Nymphaea alba, Saraca asoca, Hibiscus alba, Couroupita guianensis* and *Plumbago rosea*.

10. A method of strengthening the immune system comprising administering a therapeutically effective amount of the composition claimed in claim 1.

11. The method as claimed in claim 10, wherein said therapeutically effective amount is in the range of 100 mg and 200 mg.

12. The method as claimed in claim 10, wherein said composition is administered in the form of oral drops in an amount ranging from 1 to 4 drops.

13. The method as claimed in claim 10, wherein said composition is administered twice a day.

\* \* \* \* \*